United States Patent [19]

Velnosky et al.

[11] Patent Number: 4,529,867
[45] Date of Patent: Jul. 16, 1985

[54] HUMIDIFIER AND HEATER

[75] Inventors: Thomas E. Velnosky, Alta Loma; Raymond E. Watts, Ontario, both of Calif.

[73] Assignee: Inspiron Corporation, Rancho Cucamonga, Calif.

[21] Appl. No.: 578,424

[22] Filed: Feb. 9, 1984

[51] Int. Cl.³ .......................... F24H 1/00; F16K 21/18
[52] U.S. Cl. .................................... 219/274; 137/391; 219/272; 219/333
[58] Field of Search ........................ 261/142; 239/136; 128/203.27; 137/391

[56] References Cited

U.S. PATENT DOCUMENTS

| 1,294,551 | 2/1919 | Smethurst | 137/391 X |
|---|---|---|---|
| 2,883,511 | 4/1959 | Gooldy | 239/136 |
| 3,672,568 | 6/1972 | Foote | 261/142 X |
| 3,860,028 | 1/1975 | Moore et al. | 137/391 X |
| 4,098,573 | 7/1978 | Gunther | 261/142 X |
| 4,110,419 | 8/1978 | Miller | 261/142 |
| 4,291,838 | 9/1981 | Williams | 239/138 |

Primary Examiner—William E. Wayner
Attorney, Agent, or Firm—Spensley Horn Jubas & Lubitz

[57] ABSTRACT

This invention relates to a humidifier and associated heater. The humidifier of the present invention is for humidifying breathable gas such as air or oxygen-supplemented air to be inhaled by a patient. The humidifier comprises a body defining a humidifying chamber, a fluid inlet conduit, and a fluid outlet conduit for directing a moving stream of breathable gas into and out of the body, and a liquid collection well. A sheet of wicking material is suspended within the body and absorbs liquid in the well, exposing the liquid to the moving stream of gas as it passes through the body. The body also includes a heat exchange sleeve which extends into the collection well, the interior of the sleeve being isolated from the humidifying chamber. The heater is selectively joined to the humidifier, extends into the heat exchange sleeve and heats the humidified stream of gas as it passes through the body.

6 Claims, 8 Drawing Figures

U.S. Patent  Jul. 16, 1985  Sheet 1 of 2  4,529,867
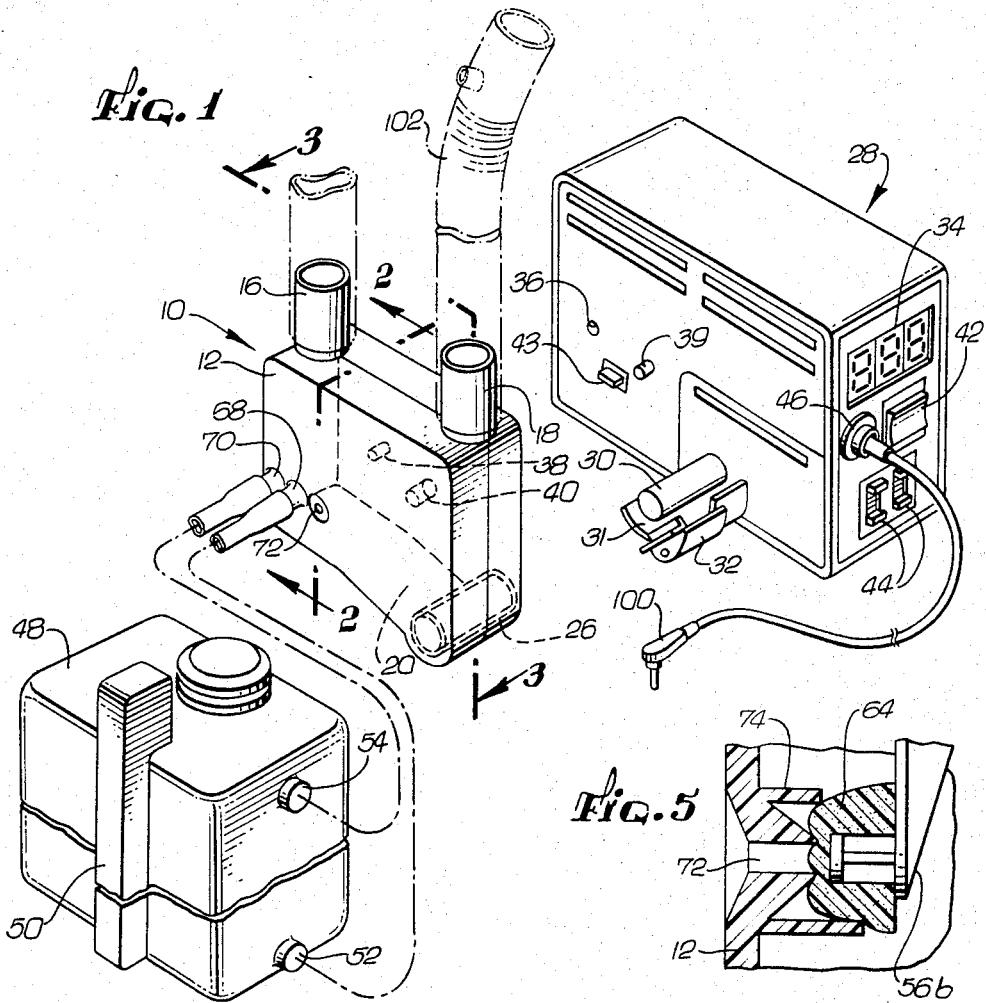
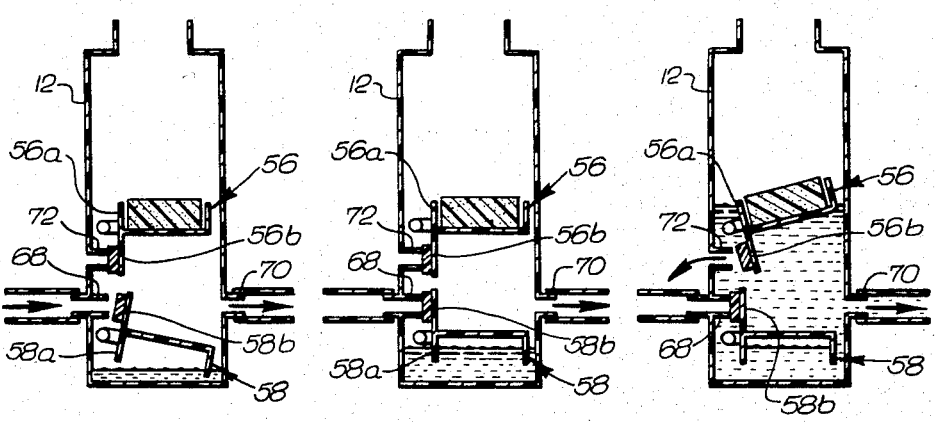

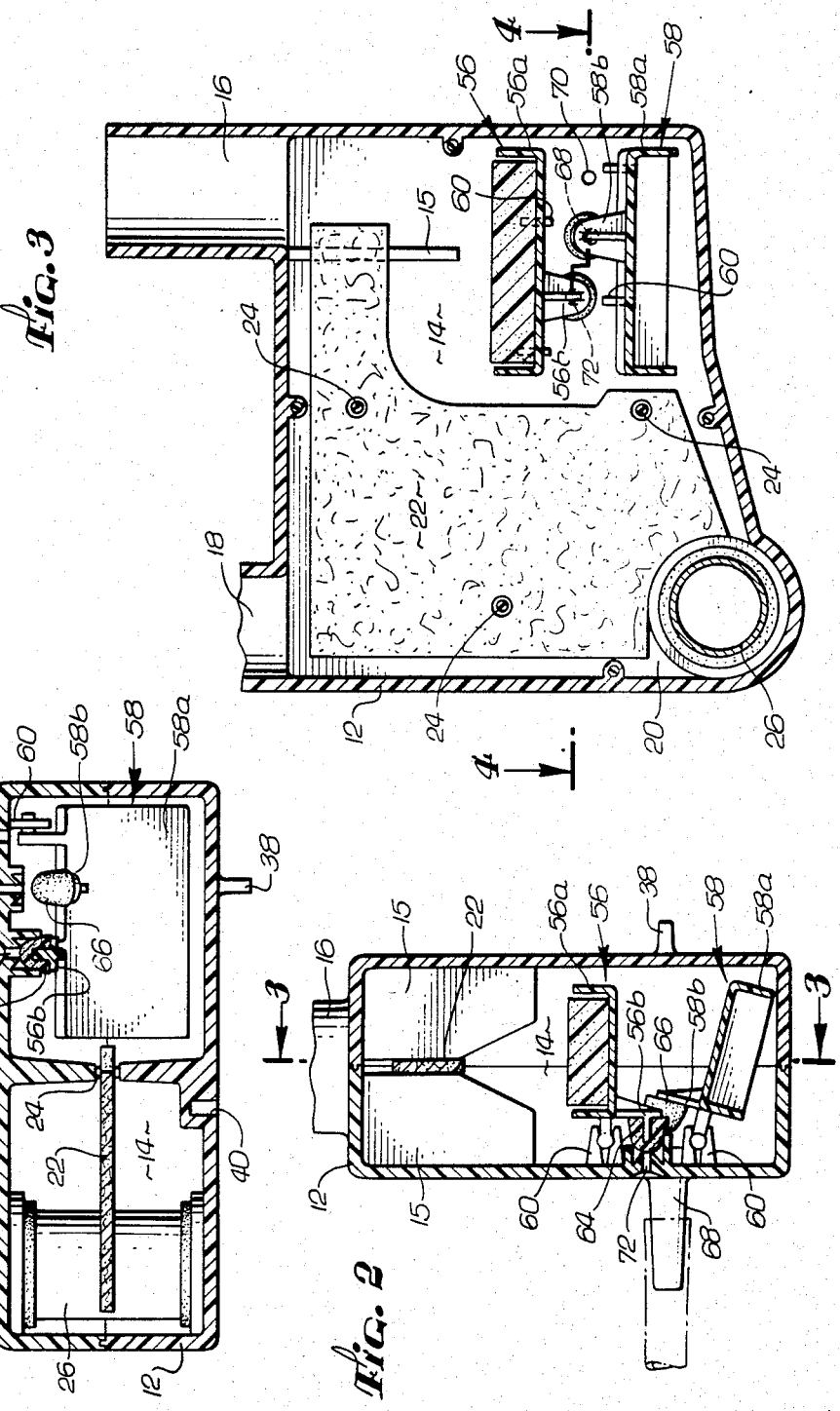

HUMIDIFIER AND HEATER

BACKGROUND OF THE INVENTION

1. Field of the Invention

The present invention relates to the field of humidifiers, and more specifically, to a humidifier and heater combination.

2. Prior Art

Humidifiers are typically used with respiratory equipment to both warm and humidify a breathable gas provided to a patient. Such gas usually consists of oxygen, air and anasthetic gas or mixtures thereof. It is also well known that where inhalation therapy is used, many components of the equipment are reusable and thus must be sterilized prior to being reused. Such prior art units are often accompanied by a number of objectionable features including the difficulty in sterilization, the inability to quickly heat the humidified gas stream and the inability to control the temperature of the gas stream delivered to the patient.

Generally, humidifiers fall into two categories, a bubble humidifier and an evaporative or pass-over type humidifier. A bubble humidifier functions by blowing air through a tube and allowing it to exit near the bottom of a water reservoir and then bubble up through the water. Since the normal rise of bubbles through a short water distance does not usually provide sufficient humidification and/or heating of the gas bubble, these units are usually equipped with baffles, porous packing or the like to break up the bubbles into smaller sizes and to slow their travel. In addition, smaller size bubbles provide for increases in humidification. Such bubble humidifiers often include complex heaters in order for the water and/or the gas stream to be heated to a desired temperature.

Evaporative humidifiers are of a more recent design and are rapidly gaining acceptance because of their advantages over bubble humidifiers. In their simplest form, evaporative humidifiers allow the gas to pick up humidity by passage of the gas over a wetted surface. Efficiency, as measured by humidity increase, can be increased by increasing the area of wetted contact either in terms of two-dimensional area or by increasing surface porocity or texture. It can be further enhanced by heating the water, directly or indirectly, or by heating the evaporative surface, or by heating the air. Notwithstanding the recognition of the advantages associated with heating, the prior art has not evolved a heater which is straight forward in its design, and which can be used on other similar equipment such as a nebulizer. Thus, even though the prior art is aware of the advantages associated with evaporative humidifiers, heater design has lagged behind.

Examples of humidifiers and similar equipment is illustrated in U.S. Pat. Nos. 4,110,419; 4,225,542; 4,201,204; 3,954,290; and 4,303,601; and 4,366,105.

From a review of these references, it can be seen that most humidifers do not readily lend itself to the use of an easily removable, compact, but efficient heater. The present invention addresses these and other problems identified above with respect to the prior art.

BRIEF SUMMARY OF THE INVENTION

The present invention relates to a humidifying device for humidifying breathable gas as well as a means for regulating the temperature of such gas. In the preferred embodiment, the humidifier portion comprises a plastic disposal body which can be easily joined to a heater. The body defines a humidifying chamber having a fluid inlet conduit and a fluid outlet conduit for directing a stream of gas into and out of the body. A liquid collection well is found at the bottom of the chamber, and a heat exchange tube and extends into the well, the interior of the sleeve being isolated from the humidifying chamber. A sheet of absorbent wicking material is suspended in the chamber and extends into the well. The wicking material absorbs the liquid in the well and draws it up thereby exposing it to the steam of gas.

The heater portion of the present invention is similar in construction to the one disclosed in U.S. Pat. No. 4,291,838, the disclosure of which is herein incorporated by reference. In the heater of the present invention, an outwardly extending heating element is inserted into the heat exchange sleeve of the humidifier. Activating the heater causes the water in the well and, in turn, the flowing gas stream to become heated.

Humidification is accomplished as water which has accumulated in the collection well of the humidifier is absorbed by the wicking material. The wicking material is partially submerged into the water, with the remainder of its surface exposed to the moving stream of gas. As the gas passes through the humidifying chamber, it picks up moisture from the wicking material according to recognized humidification principals. After the gas passes through the humidifier, it is directed to the patient. Humidification is further enhanced as the water in the reservoir can be heated to its boiling point (212° F.). This causes the flowing gas to increase in temperature. An increase in the temperature of the gas stream allows the gas to carry more moisture.

By the combination of heater and humidifier, increases in humidity levels and regulation of gas temperature as prescribed by a physician or other health care individual can be achieved. The humidifier and heater combination of the present invention can also be used in series with well known volume ventilators, or similar types of life-support machines which assist in or breathe for the patient. Broadly, the entire system is intended to perform similar functions to the nose, throat and mouth when they are bypassed such as during intubation.

The novel features which are believed to be characteristic of this invention, both as to its organization and method of operation, together with further objectives and advantages thereof, will be better understood from the following description considered in connection with the accompanying drawings in which a presently preferred embodiment of the invention is illustrated by way of example. It is to be expressly understood, however, that the drawings are for the purpose of illustration and description only, and are not intended as a definition of the limits of the invention.

BRIEF DESCRIPTION OF THE DRAWINGS

FIG. 1 is a perspective view showing the humidifier and associated heater of the present invention in an exploded view;

FIG. 2 is a cut-away view of a portion of FIG. 1, illustrating some of the internal components of the humidifier portion of the present invention;

FIG. 3 is a cut-away view of FIG. 1 showing the placement of the wicking material;

FIG. 4 is a cut-away view of FIG. 3 illustrating a portion of the liquid regulation system;

FIG. 5 is a cut-away view of a float tip and how it engages an overflow port; and FIGS. 6, 7 and 8 further illustrate the liquid regulation system of the present invention.

DETAILED DESCRIPTION OF THE INVENTION

Referring first to FIGS. 1, 2 and 3, the humidifying apparatus 10 of the present invention is illustrated. The apparatus 10 comprises a plastic body 12 defining a humidifying chamber 14 and having a fluid inlet port 16 and a fluid outlet port 18. An integral liquid collection well 20 is disposed adjacent the bottom of the humidifying chamber 14, and is used to collect and store liquid as hereinafter described in greater detail. An absorptive sheet 22 of wicking material is suspended within body 12 by a plurality of pin members 24. By this method of suspension, a large area of sheet 22 is exposed to the stream of gas as it flows through body 12.

Extending transversely through the body 12 and across the collection well 20 is a metallic sleeve 26. A pair of water tight, heat resistant silicon rubber washers are disposed about each end of sleeve 26, and are placed in a depressed region formed in the side walls of well 20. In this manner, sleeve 26 is held in position.

As illustrated in FIG. 1, a heater 28 can be readily joined to the humidifying apparatus 10. As stated above, the heater 28 of the present invention is similar to that illustrated in U.S. Pat. No. 4,291,838, and contains a number of desirable features. For example, heater 28 has an outwardly extending, cylindrical heating element 30 arranged and configured so as to be slidably disposable within metal sleeve 26. A plastic safety guard 31 is provided adjacent element 30 to prevent inadvertent touching by a user. Guard 31 fits the contour of the well 20 and includes a springloaded latch 32. When the latch 32 is depressed, the heating element 30 can be slipped into sleeve 26. Once fully within the sleeve 26, latch 32 engages a portion of the body 12 adjacent well 20. Heating element 30 is controlled by an electronic temperature control system similar to that disclosed in the '838 patent. While a single thermostat can be used to regulate the temperature of the liquid in well 20, the control system of the present invention employs a system which controls the temperature of the humidified gas stream actually delivered to the patient. In some prior art heaters, the temperature of the water in the humidifier was controlled; however, the temperature actually delivered to the patient could be lower. In the present invention, a thermistor probe 100 is positioned in an opening located near the patient end of gas delivery conduit 102. The probe 100 is detachably connected to a socket 46 located in the body of heater 28, and can be used to determine the temperature of the gas stream just prior to the patient. A digital temperature indicator 34 which displays the patient airway temperature as detected by the thermistor probe 100 is provided on the heater 28. The desired patient airway temperature can be controlled by setting digital temperature select switches 44.

An opening 36 is specifically positioned on heater 28 such that an integrally molded extension or similar element 38 extending from body 12 will fit into open 36 when the heater 28 is properly abutting against body 12. Also located within heater 28 adjacent opening 36 is a switch which can identify the presence or absence of extension 38. In this manner, the heater "knows" when it is in proper position with respect to the humidifier 10. Activation of the switch causes certain functions of an internally located microprocessor to become operational. Switches of this type are conventional and will not be discussed in detail. An outwardly extending overtemperature sensor 39 is also provided on heater 28 and enters into opening 40 formed on body 12 so as to determine internal operational temperatures within chamber 14. In addition, sensor 39 helps encourage proper alignment of the heater 28 and humidifier 10. The heater 28 also includes an on/reset standby power switch 42, and an interlock switch 43. Switch 43 is positioned on heater 28 such that when the humidifier 12 or a nebulizer is joined to the heater 28, a signal is sent to the microprocessor. This enables one to control heating element 30.

Also illustrated in FIG. 1 is a bottle 48 having an external conduit 50 such as is illustrated in the '838 patent. Bottle 48 has been modified by providing a water port 52 adjacent the bottom and an air or gas port 54 adjacent the top thereof. In this manner, liquid can be delivered to the humidifier 10 without interruption even though there may be pressure variances in the system. Further, the bottle used in connection with the nebulizer illustrated in the '838 patent can be used in the humidifier and heater combination of the present invention.

In operation of the present invention, bottle 48 containing a sterile water supply is placed in a predetermined proximity to the humidifier 10. The bottle 48 has two puncture sites at the top ½ inch and the bottom ½ inch. On centerline, water flows by gravity from the bottom puncture site defined by water port 52 through a bayonet fitting and vinyl tube to the humidifier 10. A second return vent tube is connected from the top puncture site defined by gas port 54 through a bayonet fitting and vinyl tube of a smaller diameter back to the humidifier 10. In the preferred embodiment, gas port 54 is joined to humidifier 10 above a predetermined water level. This allows for constant pressure equalization between the ventilator circuit/humidifier 10 and the air in the bottle 48, a distinct advantage as differences in pressure can prevent proper water level control.

The water level in the humidifier 10 of the present invention is controlled by first and second generally rectangular box-like floats 56, 58, which form a portion of the liquid regulation system. Basically, floats 56, 58 are comprised of a float body 56a, 58a and a float tip 56b, 58b. The float body 56a, 58a is made of an expanded polystyrene plastic. Float tips 56b, 58b are made of a low shore silicon elastomer, although other materials are also within the scope of the present invention. After the floats are assemble, they are placed in the humidifier 10 in a movable position by means of slotted arms 60. As illustrated in FIGS. 2 and 3, tip 58b engages port 68 which is in flow communication with water port 52. Tip 56b, in turn, engages safety port 72, described in greater detail below. To help insure that flow through ports 68 and 72 takes place when desired, circumferential float seats 74 are provided. The interaction of seats 74 on the float tips 64, 66 is illustrated in FIG. 5. As shown in FIG. 3, port 70 is left open thus enabling pressure changes in body 12 to readily take place and also to act as an overflow.

When water flows into the humidifier 10, it is uninterrupted and the well 20 soon fills. Filling continues until the water level reaches the point where float 58 is lifted up, causing the float tip 58b to seal the water inlet port 68 as illustrated in FIGS. 6 and 7. As the water is absorbed and consumed during normal operation, the float 58 allows in only the amount of water as is required to maintain the desired level.

Inasmuch as gravity is used to fill the humidifier 10, it is possible in the event of a float failure, that the humidifier could overfill from the water supply. In order to prevent this, a secondary float 56 is used. The secondary float 56 is identical to the primary float 58, but is mounted upside down so that the weight of the float 56 during normal operation maintains a seal on the safety outlet port 72. In the event of a primary float failure, the water level will rise causing the secondary float to lift up, thereby opening the outlet port 72. This will allow excess water to be expelled from the humidifier 10. This is also encouraged as excess water can escape back to the bottle 48 through port 70.

Normally, sheet 22 is made of a non-woven polyester fabric having a thickness of about 0.094 in. This has been found to be a good wicking material, although other materials are within the scope of this invention. Sheet 22 is partially submerged in the water below the controlled water level, and water is wicked up and exposed over the entire flat sheet 22 which provides an enlarged surface area of moisture for the gas travelling through the humidifier 10. This action is encouraged by centrally suspending sheet 22 such that both sides of the sheet 22 are exposed to the gas stream. As gas enters humidifier 10 through inlet port 16, it flows through humidification chamber 14. This is encouraged by baffles 15 which help direct the gas toward the bottom of the chamber 14 in order to maximize gas exposure to sheet 22. As the gas is exposed to wetted sheet 22, water is transferred to the gas stream by well-recognized humidification principles.

As illustrated in FIG. 1, heater 28 can easily be joined to the humidifier 10 when desired. In operation, the temperature of the delivered humidified gas as determined by the thermistor probe 100 is compared to the temperature set on the digital temperature select switches 44 by means of a digital comparison made by the microprocessor. If the temperature of the delivered humidified gas is lower than the set temperature, the microprocessor will cause the heating element 30 to energize. The heating element 30 remains energized until the temperature of the delivered humidified gas is equal to the set temperature.

The heater 28 also includes several features designed for patient protection. If the humidified gas temperature, as measured by thermistor probe 100, exceeds a set temperature, current to the heating element 30 will automatically be removed. This is done by using special software commands programmed into the microprocessor. Similarly, overtemperature sensor 39, located at the rear side of the heater 28, is used to detect operational temperatures in chamber 14. If the operational temperatures in chamber 14 exceed a predetermined value, sensor 39 will relay this to the microprocessor. In turn, the microprocessor will deenergized element 30.

A third safety mechanism consists of the safety interlock switch 43. As discussed above, such switch 43 is engaged by the body of the humidifier 10 (or nebulizer) when heater 28 is properly affixed.

A fourth safety mechanism causes power to the heating element 30 to be interrupted if the core of the heating element 30 rises above a predetermined value. If the well 20 runs dry, the temperature of the heating element 30 will quickly rise. A core thermocouple determines the temperature of the core of the heating element 30. Again, the microprocessor is utilized to remove power to heating element 30, if a predetermined temperature is exceeded.

Yet another safety mechanism causes interruption of power to the heating element 30 should certain central devices in the heater 28 malfunction.

Thus, the heater 28 controls the temperature of the humidified gas which is actually delivered to the patient, rather than the stream which leaves the humidifier 10. In addition, the heater 28 includes a number of safety shutoff mechanisms which remove power to the heating element 30. After removal of power, a reset switch on the heater body must be activated to enable power to again be supplied to the heating element 30.

Heat from the heating element 30 is transmitted by conduction through the tubular sleeve 26, which in turn heats the pool of liquid in the collection well 20. As the gas stream passes over the heated liquid, it is heated by hot liquid vapor before flowing out through the outlet conduit 18. After flowing out of the humidifier 10, the heated and humidified gas stream is directed to the patient by conduit 102.

Yet another advantage of the heater 28 of the present invention is that it can also be used in conjunction with the nebulizer illustrated in the '838 patent. That is, heater 28 is designed such that when joined to humidifier 10, certain software commands are activated and used, and when joined to the '838 nebulizer other software commands are activated and used. This is achieved by the use of the internal microprocessor, certain software commands of which are activated by means of pin 38 entering opening 36 and activating a switch. When such switch is not activated, a signal is not sent to the microprocessor and the heater functions in a manner appropriate for a nebulizer.

It should be understood that while the preferred examples described relate to certain shapes and materials, other configurations and materials can be used. In addition, it will also be apparent to one who is skilled in the art that other changes and modifications can be made without departing from the spirit or scope of the present invention as defined and claimed herein.

What is claimed is:

1. A humidifying apparatus for humidifying a breathable gas such as air or oxygen-supplemented air to be inhaled by a patient, comprising:
   (a) a body defining a humidifying chamber, a fluid inlet conduit and a fluid outlet conduit for directing a breathable gas stream into and out of the body, and a liquid collection well;
   (b) a sheet of wicking material centrally suspended within said body, for absorbing a liquid in said well and exposing said liquid to said moving stream of gas as it passes through said body;
   (c) a heat exchange sleeve extending into said collection well, the interior of said sleeve being isolated from the humidifying chamber;
   (d) said body having a liquid inlet pipe extending into said body for selectively permitting liquid to flow into said collection well, and a safety outlet pipe extending into said body for selectively permitting liquid to flow out of said body;
   (e) a pivotally mounted first float valve consisting of a substantially horizontal platform, and a leg portion substantially perpendicular to said platform, said leg portion having an elastomer material mounted thereon such that said material is adjacent the liquid inlet pipe, whereby when fluid in said collection well rises to a first predetermined level said first float valve pivots thereby bringing the elastomer material into contact with the liquid inlet pipe and sealing the mouth of said pipe; and (f) a pivotally mounted second float valve consisting of a substantially horizontal platform, and a leg portion substantially perpendicular to said platform, said leg portion having an elastomer material mounted thereon such that said material is adjacent the safety outlet pipe and normally seals the adjacent mount portion of the safety outlet pipe except when fluid in said fluid collection well rises to a second predetermined level which is above the first predetermined level, said second float valve pivots thereby bringing the elastomer material out of sealing contact with the adjacent mouth portion of the outlet pipe and permitting fluid to flow out of said humidifying chamber.

2. The humidifying apparatus set forth in claim 1 wherein said collection well is integrally formed on and depends from said body, and said absorbing means extends into said well.

3. The humidifying apparatus set forth in claim 1 wherein said means for absorbing a liquid comprises a sheet of wicking material centrally suspended within said body.

4. The humidifying apparatus set forth in claim 1 further including a heater detachably secured to said body, said heater including a heating element extending into and contacting said sleeve thereby heating the liquid collected in the well.

5. The humidifying apparatus set forth in claim 4 further including temperature regulating means for controlling the temperature of the heating element.

6. The humidifying apparatus of claim 5 wherein the temperature regulating means includes remote measurement means for determining the temperature of the humidified air delivered to a patient, and wherein the temperature of the heating element is regulated in response to said determined temperature.

* * * * *